(12) United States Patent
Obeid et al.

(10) Patent No.: US 8,383,047 B2
(45) Date of Patent: Feb. 26, 2013

(54) FIBRE OPTIC SENSOR

(76) Inventors: Andrew Obeid, Oxford (GB); Neville Davies, Oxford (GB); Suzanne Douglas, Pinner (GB); Trevor DuPlooy, Bicester (GB); Geoffrey Ward, Warrnambool (AU)

( * ) Notice: Subject to any disclaimer, the term of this patent is extended or adjusted under 35 U.S.C. 154(b) by 1028 days.

(21) Appl. No.: 11/908,105

(22) PCT Filed: Mar. 13, 2006

(86) PCT No.: PCT/GB2006/000868
§ 371 (c)(1),
(2), (4) Date: Oct. 29, 2008

(87) PCT Pub. No.: WO2006/095191
PCT Pub. Date: Sep. 14, 2006

(65) Prior Publication Data
US 2009/0075321 A1 Mar. 19, 2009

(30) Foreign Application Priority Data
Mar. 11, 2005 (GB) .................................. 0505036.4

(51) Int. Cl.
*G01N 21/01* (2006.01)
*G01N 21/64* (2006.01)
*G01N 21/62* (2006.01)
*G01N 31/00* (2006.01)
(52) U.S. Cl. ..................................... 422/82.06
(58) Field of Classification Search .......... 422/62, 422/68.1, 82.05, 82.08, 83, 88, 91; 436/164, 436/167, 172, 800, 805, 807; 435/288.7, 435/808; 73/19.01, 19.1; 702/24; 356/73.1
See application file for complete search history.

(56) References Cited

U.S. PATENT DOCUMENTS
3,138,937 A * 6/1964 Parkinson et al. .............. 62/100
(Continued)

FOREIGN PATENT DOCUMENTS
EP 0336985 A1 10/1989
WO WO9219150 * 11/1992
(Continued)

OTHER PUBLICATIONS
Wolfbeis, Otto S., "Fibre-optic chemical sensors and biosensors," Analytical Chemistry, 2004, 76, pp. 3269-3284.

*Primary Examiner* — Neil N Turk
(74) *Attorney, Agent, or Firm* — McDonnell Boehnen Hulbert & Berghoff LLP

(57) ABSTRACT

A sensor for measuring the concentration of an assay substance, such as oxygen in tissue. The sensor comprises an optical fiber (2) which passes through, a gas isolation collar (11) into a cavity (15) defined by a needle tube (13) attached to the gas isolation collar. Both the optical fiber (2) and the needle tube (13) are bonded to the gas isolation collar (11) in gas-tight fashion. The cleaved end (8) of the optical fiber within the cavity is provided with an optically active substance (9) having optical properties, such as fluorescence, dependent on the concentration of the assay substance. The cavity (15) is filled with a polymer (16) which is permeable to the assay substance. Lateral flow passages (18) are provided for the assay substance to pass into the permeable polymer (16) and to the fluorophor (9). Light is supplied to the fluorophor via the optical fiber, and functions of its fluorescence are measured to calculate the concentration of the assay substance.

30 Claims, 4 Drawing Sheets

U.S. PATENT DOCUMENTS

| | | | |
|---|---|---|---|
| 4,727,730 A * | 3/1988 | Boiarski et al. | 600/480 |
| 4,784,811 A * | 11/1988 | Hirschfeld | 264/1.27 |
| 5,005,576 A * | 4/1991 | Gunther | 600/311 |
| 5,037,615 A | 8/1991 | Kane | |
| 5,047,208 A * | 9/1991 | Schweitzer et al. | 422/402 |
| 5,054,882 A * | 10/1991 | Riccitelli et al. | 385/12 |
| 5,119,463 A * | 6/1992 | Vurek et al. | 385/129 |
| 5,173,432 A * | 12/1992 | Lefkowitz et al. | 436/138 |
| 5,328,823 A * | 7/1994 | Spencer et al. | 435/4 |
| 5,333,609 A * | 8/1994 | Bedingham et al. | 600/339 |
| 5,353,792 A * | 10/1994 | Lubbers et al. | 600/311 |
| 5,408,999 A * | 4/1995 | Singh et al. | 600/342 |
| 6,328,932 B1 * | 12/2001 | Carter et al. | 422/82.06 |
| 6,531,097 B1 * | 3/2003 | Vojnovic et al. | 422/82.07 |

FOREIGN PATENT DOCUMENTS

WO     WO 9219150 A     11/1992

* cited by examiner

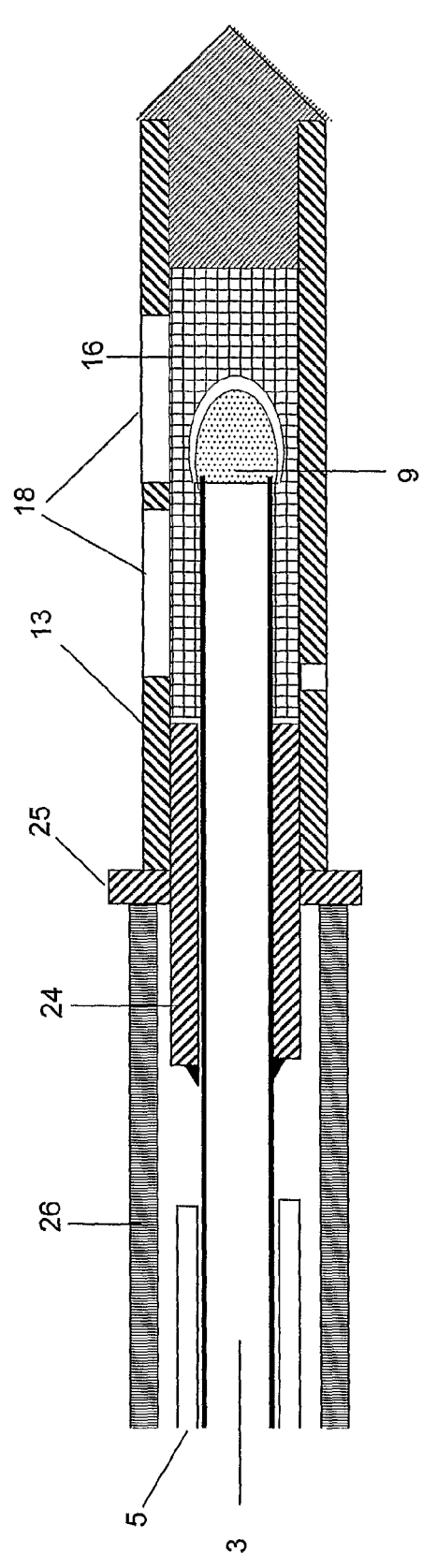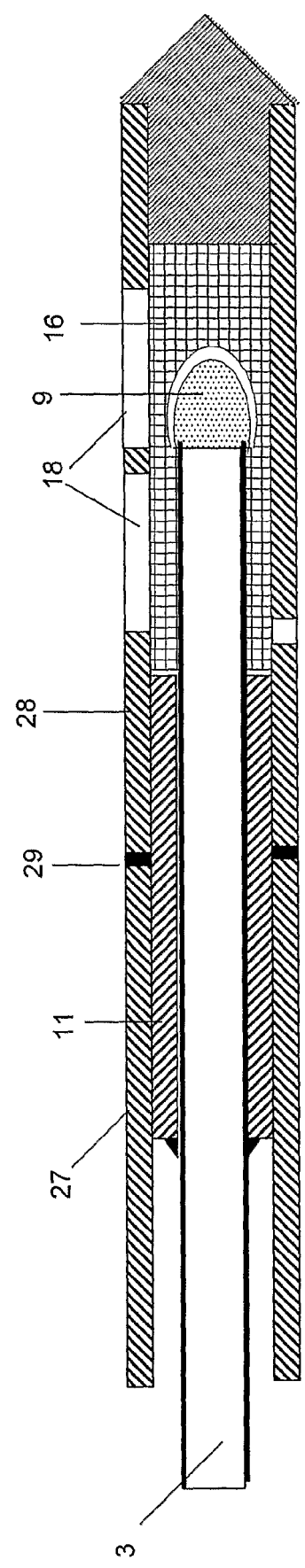
Figure 6
Figure 7

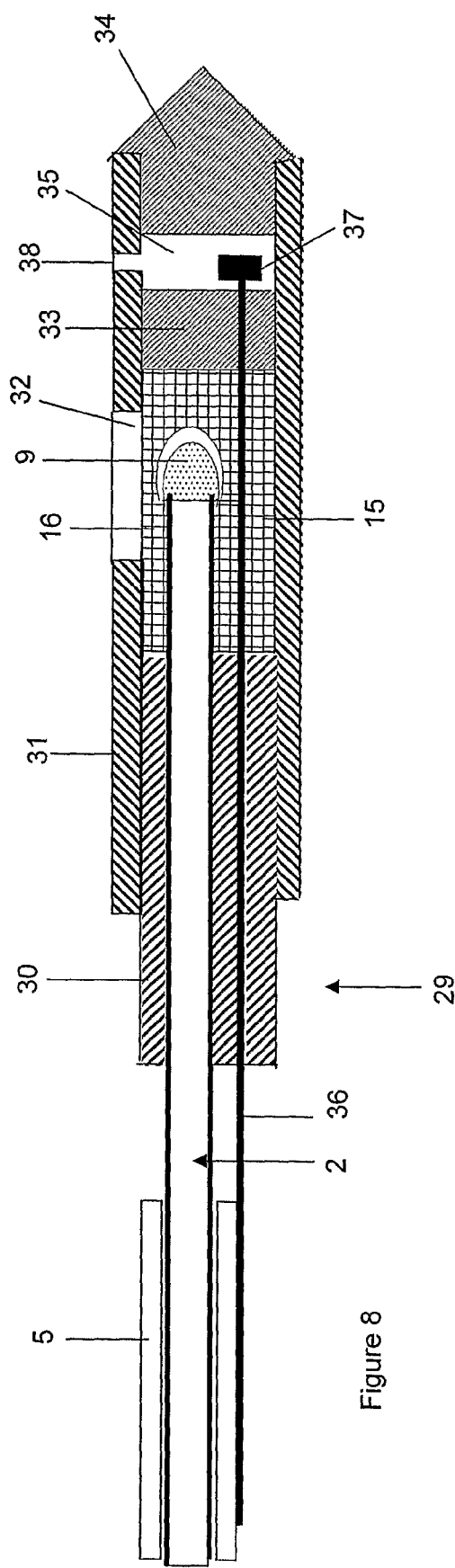
Figure 8
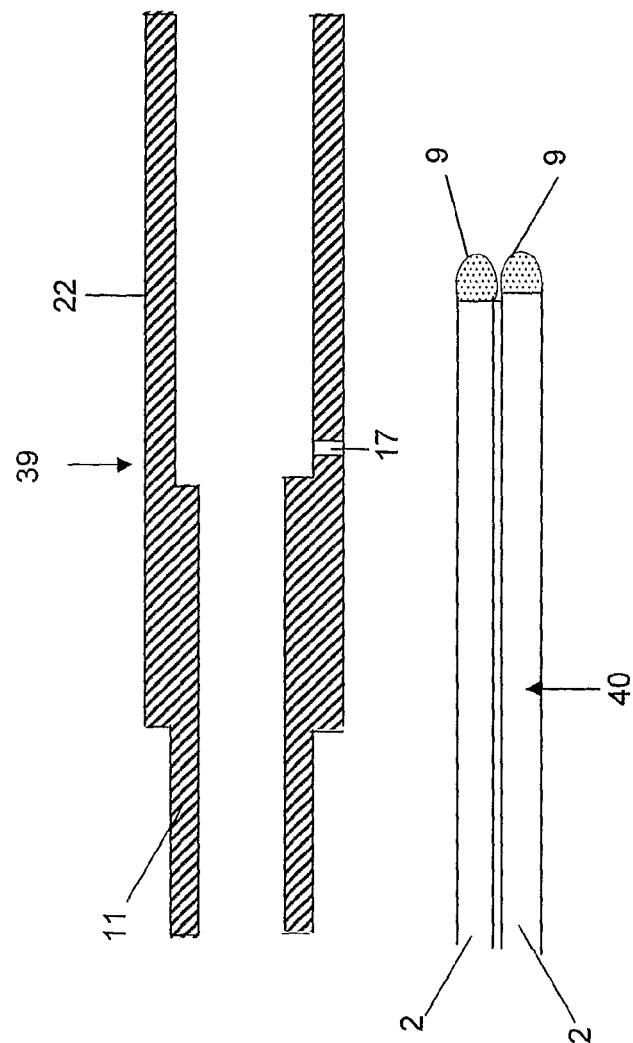
Figure 9
Figure 10

FIBRE OPTIC SENSOR

This application is a National Stage application of International Application No. PCT/GB2006/000868 filed on Mar. 13, 2006 which published as WO 2006/095191 on Sep. 14, 2006, and claims priority to Great Britain Application No. 0505036.4 filed Mar. 11, 2005.

BACKGROUND OF THE INVENTION

1. Field of the Invention

The present invention relates to the measurement of the concentration of substances, and particularly but not exclusively to the measurement of the concentration of substances such as oxygen, for example, in human or animal tissue.

2. Description of Related Art

The survival of tissue cells relies on an adequate supply of oxygen to the mitochondria within the tissue cells. Over recent years, several technologies have been developed for monitoring oxygenation at the different stages of oxygen transport from the outside environment to tissue cells. Most importantly, the measurement of oxygen partial pressure in tissue ($PtiO_2$) has provided a measure of oxygen availability at the cellular level.

Polarographic (redox based) electrodes have been widely used for monitoring tissue oxygen but a number of disadvantages remain unresolved. The fundamental problem at low oxygen pressures is that the electrodes consume a significant quantity of oxygen by the electro-chemical reduction reaction. As a result, the electrode tends to underestimate the level of tissue oxygen—an effect which is most evident under conditions of tissue hypoxia. Other reported problems concern long-term stability and measurement drift. Routine calibration is required to compensate for drift and the calibration procedure itself is frequently a complex and time-consuming process.

Recently, tissue oxygen sensors based on new-generation optical technology for continuous quantitative monitoring of regional $pO_2$ in tissue and fluids have been developed. These oxygen sensors are based on the property of certain chemical compounds (luminophores) to produce an 'afterglow' or 'luminescence' when they are illuminated and stimulated with a short burst of light. The duration of this luminescence signal is related to the amount of oxygen present in the vicinity of the luminophor dye compound and typically lasts for only a few millionths of a second but nevertheless is long enough to be able to detect it reliably using modern optoelectronic devices.

Typically, short pulses of (e.g. green or blue) light are transmitted along a fibre to excite a luminophor situated at the fibre tip. The luminophor is usually immobilised within a polymer matrix or solgel. Following excitation, the resulting emission of the (longer wavelength) luminescent light, quenched by the presence of oxygen molecules, travels back up the fibre and is detected by an appropriate instrument. The decay lifetime of the luminescence (typically microseconds) is inversely proportional to the concentration of dissolved oxygen, and is electronically processed to provide an absolute value for $pO_2$ in mm Hg, kPa or Torr.

Luminescence lifetime is longest at low oxygen partial pressures making such sensors very sensitive in the physiological range 0-150 mmHg. This makes them particularly suited to measuring regions of hypoxia in tissue; in contrast to all other types of sensor. Since luminescence-based sensors do not show significant oxygen consumption, these sensors can not only be used to gain spatial $pO_2$ information, but can be left in situ for monitoring the long-term, temporal evolution in tissue $pO_2$. Additionally, when such systems are based on luminescence lifetime rather than luminescence intensity, they are much less prone to artefacts (e.g. due to variation in the intensity of the light source, ambient lighting, photobleaching etc.).

A discussion of fibre optic chemical sensors may be found in "Fibre-Optic Chemical Sensors and Biosensors" by Otto S. Wolfbeis, Anal. Chem. 2004, 76, 3269-3284, the contents of which are incorporated herein by way of reference.

The difficulties of developing a practical fibre-optic oxygen sensor for clinical application are considerable. Optical-fibre-only oxygen sensors based on a simple, bare, fibre-optic construction are largely unsuitable for human in-vivo (e.g. clinical) application—because they are fragile, difficult to insert and in a single-fault condition may expose the patient to unacceptable risks. These include the risk of broken optical fibre (silica) entering the blood stream as a result of breaking in situ and/or the risk of the sensing tip becoming detached from the sensor and itself entering the blood stream or implanting in tissue.

One arrangement for measuring the concentration of oxygen is disclosed in U.S. Pat. No. 6,531,097, which is incorporated herein by way of reference. A sensor comprises an optical fibre. At one end of the fibre, the buffer layer is stripped away to leave the fibre and its cladding. The end of the fibre is coated with a body of moulded polymer in which are disposed silica particles containing a fluorescent dye such as tris4,7-diphenyl-1,10-phenanthroline)Ru(II)Cl. That body and the remainder of the fibre and its cladding, up to the buffer layer, are provided with a protective coating of the same polymer, without the silica gel particles. In one embodiment, a rigid needle of metal or ceramic is provided over the fibre and its cladding back to the buffer layer, and is also sealed to the buffer layer. This is said to improve robustness. In the embodiment described and illustrated, the end of the fibre and its dye containing body and protective polymer coating are exposed. It is said that the end of the fibre may be enclosed within the bore of the needle, although no further details are given.

A potential problem associated with known fibre-optic sensors, including that in U.S. Pat. No. 6,531,097, is that the measurement site is at the very tip (or distal end) of the fibre, which is also in the region at which maximal tissue trauma occurs (due to mechanical insertion) as well as being the region at which the tissue is most occluded (due to mechanical compression). These effects can combine to cause undesirable measurement artefacts. In addition, in most types of tissue, oxygen values can vary markedly from one micro region to the next. As a result the measurement can be very sensitive to the precise positioning of the tip, and to movements which may alter that positioning, including breathing, blood flow and so forth. Readings may fluctuate even when a patient is kept as stationary as possible.

SUMMARY OF THE INVENTION

Viewed from one aspect, the present invention provides a sensor for measuring the concentration of an assay substance, the sensor comprising an optical fibre which extends longitudinally into a cavity defined by a surrounding wall, the optical fibre having an end portion within the cavity, and the end portion terminating in a tip which is provided with an optically active substance which has optical properties which depend on the concentration of the assay substance; wherein the cavity is filled with an encapsulating material which is permeable to the assay substance and which encapsulates the end portion of the optical fibre, and the surrounding wall is provided with at least one laterally directed flow path for communicating the cavity with a region to be sampled.

In this manner, the region from which the assay substance is sampled can be displaced from the end of the sensor, which in the case of taking samples from patient tissue will normally be situated in a region of maximum tissue trauma. Furthermore, the area from which the assay substance can be sampled is not restricted to the end cross section of the sensor. The total effective cross section of one or more lateral flow paths through the wall of the cavity can exceed the cross section of the sensor. However, even if the effective cross-section is not increased the displacement of the sensing region from the end of the sensor has advantages, and the filling of the cavity with the encapsulating material will avoid problems such as tissue or other impurities entering the cavity and affecting readings. The encapsulating material provides a controlled environment within the cavity.

The cavity is preferably elongate.

In some preferred embodiments at least one aperture is formed in an impermeable wall of the cavity to provide the flow pat. The aperture is preferably in the form of an elongate slot, although a series of e.g. circular or square cross section apertures could also be used. Preferably, a number of apertures are provided, spaced around the periphery of the wall of the chamber. In one arrangement there are three aperture regions spaced equally around the circumference of the wall, each aperture region comprising a pair of aligned elongate slots extending longitudinally. However, the precise number, shape and arrangement of apertures can be chosen as desired.

Alternatively, the flow path(s) communicating the cavity with the regions to be sampled could be provided by one or more permeable regions of an impermeable wall of the cavity, or the entire wall could be permeable.

It is possible for the distal end of the chamber to be open, thus additionally enabling sampling from a region at the end of the sensor.

As noted above, the use of one or more flow paths through the wall of the cavity can provide sampling regions extending over an area which is substantially greater than the cross sectional area of the end of the sensor. The arrangement will effectively integrate or average readings from the various regions. Assay samples from the various regions will pass into the permeable encapsulating material in the cavity and move to the end portion of the optical fibre. If the distal end of the cavity is open, the use of samples received from other regions where there is less tissue trauma will tend to reduce distortion of readings due to tissue trauma adjacent the end of the sensor.

In general, the total area exposed to the regions to be sampled will govern the total reading obtained using the sensor, whilst the volume of the cavity will affect the response time. In fact this will depend primarily on the volume of permeable encapsulating material within the cavity, i.e. the volume of the cavity less the volume of the components within it, namely the end portion of the optical fibre.

In any event, the provision of the permeable encapsulating material within the cavity provides a protective and controlled environment for the fibre optic and is useful even in arrangements in which there are no lateral flow paths for sampling and the assay substance is received only by the end of the sensor.

Thus, viewed from another aspect, the present invention provides a sensor for measuring the concentration of an assay substance, the sensor comprising an optical fibre which extends longitudinally into an elongate cavity which is defined by a surrounding wall and has an open end remote from that through which the optical fibre passes, the optical fibre having an end portion within the cavity which is spaced a substantial distance from the open end, and the end portion including a tip which is provided with an optically active substance whose optical properties are dependent on the concentration of the assay substance, wherein the cavity is filled with an encapsulating material which is permeable to the assay substance.

Preferably, the portion of the optical fibre is spaced from the surrounding wall of the cavity, so that some of the encapsulating material which fills the cavity and surrounds the end, is disposed between that end portion of the optical fibre and the wall of the cavity.

It will be appreciated that in some arrangements it may not be necessary for the encapsulating material to fill the cavity entirely, although total filling of the cavity is preferred.

To provide a controlled environment to ensure accurate readings, it is important that the assay substance passes into the cavity through the designated points, i.e. lateral apertures and/or an end opening. Unwanted substances which may affect readings, including the assay substance itself but obtained from an unwanted region such as the ambient atmosphere or another area of the tissue, must be excluded from the cavity. The cavity, into which the end portion of the fibre optic passes, must be sealed against such unwanted substances.

Typically, a fibre optic comprises a bare glass fibre, a thin cladding layer of a material such as silica, and a more substantial buffer layer. Substances may migrate along the buffer and could thus enter the cavity where sensing takes place. Thus, in a preferred arrangement, the buffer layer is removed from the optical fibre, so as to leave a terminating length of optical fibre. A gas isolation collar is bonded to the terminating length of optical fibre at a position remote from the remaining buffer layer, so that permeation of substances from the buffer layer, past the collar is substantially reduced or eliminated. In general, the collar will be bonded to the cladding layer and/or to the glass fibre itself.

Viewed from another aspect, the present invention provides a sensor for measuring the concentration of an assay substance, the sensor comprising an optical fibre which extends longitudinally through a base wall into a cavity which is defined by a surrounding wall, the optical fibre having an end portion enclosed within the cavity which includes a tip provided with an optically active substance whose optical properties are dependent on the concentration of the assay substance, wherein the optical fibre comprises a glass fibre, a cladding layer around the glass fibre and a buffer layer around the cladding layer, wherein the buffer layer is removed over an end region of the optical fibre, a gas isolation collar is bonded in sealing fashion to the cladding and/or glass fibre at a position remote from the remaining buffer layer, the gas isolation collar terminating short of the end portion of the optical fibre, and a tubular member is bonded to the gas isolation collar, so that the end of the gas isolation collar provides the end wall of the cavity through which the end portion of the optical fibre passes in sealing fashion, and the tubular member provides the surrounding wall defining the cavity in which the end portion of the optical fibre is enclosed.

Viewed from a further aspect, the present invention provides a sensor for measuring the concentration of an assay substance, the sensor comprising an optical fibre having an end region which extends longitudinally through a base wall into a cavity which is defined by a surrounding wall, the distal portion of the end region of the optical fibre which is enclosed within the cavity including a tip provided with an optically active substance whose optical properties are dependent on the concentration of the assay substance, wherein the end region of the optical fibre consists of material which is impermeable, a gas isolation collar is bonded in sealing fashion to a proximal portion of the end region, and a tubular member is bonded to the gas isolation collar, so that the end of the gas isolation collar provides the end wall of the cavity through which the end region of the optical fibre passes in sealing fashion, and the tubular member provides the surrounding wall defining the cavity in which the distal portion of the end region of the optical fibre is enclosed.

Preferably, the cavity is filled with an encapsulating material which is permeable to the substance being assayed. However, it should be noted that the encapsulating material may comprise permeable and impermeable components, particularly if the cavity volume is large and the response time would be excessive if filled totally with the permeable component. The permeable component could be a polymer and the impermeable component could, for example, be silica, glass or a metal.

In a preferred arrangement, an elongate gas isolation collar is provided, and an elongate tubular body has a first section which is bonded to the gas isolation collar and a second section projecting beyond the gas isolation collar which provides the surrounding wall of the cavity. The tubular body may be in the form of a needle tube and may have a solid end portion, e.g. bevelled, to provide a needle tip, or be open. A second elongate tubular body may be bonded to the proximal end of the elongate gas isolation collar, to provide additional strength. The two tubular bodies may be bonded together.

The purpose of the isolation collar is to effect a gas seal at the distal (sensing end) of the fibre-optic and provide a mechanical means of mounting extraneous components for the construction of a sheath around the sensor. The isolation collar substantially isolates gas transport from the back of the collar to the sensing area forward of the collar. The isolation collar may be a precision machined component manufactured from a material impermeable to the gas or ions in question. For example, an oxygen impermeable seal can be fashioned from a metal, ceramic or other oxygen impermeable material.

The choice of the permeable material to fill the chamber depends on the nature of the assay substance. Typically, for $pO_2$ information the material may be a silicone elastomer of a type used for encapsulation, such as MED-6010 from NuSil Technology, Carpinteria, Calif. 93013, United States of America. For ionic permeability measurement, a hydrogel may be appropriate.

In preferred embodiments, the invention provides a new type of probe that is both robust enough for clinical application and allows for precise control over the location and size of the active sensing area or volume. The sensing area can for example be located away from the point of maximal trauma as described above. In some embodiments, the new probe makes it possible to 'integrate' or 'average' large area/volume measurements via fibre optic sensing. This is particularly desirable in the case of clinical oxygen measurement, since in most types of tissue oxygen values can vary markedly from one micro region to the next. In preferred embodiments, various elements therefore combine to provide a new type of sensor for clinical measurement which is practical, accurate and safe to use with MRI scanners.

In preferred embodiments in accordance with the invention, robustness and means for measurement control are achieved by providing a well secured physical volume around the normal sensing tip chemistry of the optical fibre. This physical volume is characterised by a mechanical/environmental barrier containing a polymer based compound which is permeable to an ion or gas being measured. The polymer based compound encapsulates the normal sensing tip chemistry located at the distal end of the fibre optic.

The surrounding wall of the cavity provides a mechanical barrier and is selected to be either permeable or impermeable. By having a basically impermeable barrier, apertures or permeable regions in that barrier can be designed to locate the sensing area anywhere around the surface area of the physical volume. Furthermore, by selecting the area of aperture(s) or permeable region(s), the probe will make integrated or averaged readings over that exposed aperture area. In this way it is possible to optimise the sensing area/volume of the sensing measurement and overcome or at least alleviate the problems described above. In general, it is the effective area of a flow path—such as an aperture or permeable region—exposed to e.g. the tissue that governs the readings obtained, rather than the internal configuration of the flow path.

The ability to locate the sensing area(s) anywhere desired, makes it possible to have a sensor which is directional about its axis. If sensing takes place only over one angular segment, that can be placed against tissue to be sampled, and there will be no sensing over the remaining angular extent around the axis of the sensor. If, for example, the sensor is inserted through a cannula, that could be oriented in a particular way and be provided with a marking so that the sensor can be aligned by means of a similar marking which indicates the position of the sensing segment, or be profiled so that the sensor can only be received in a particular angular orientation.

A sensor in accordance with the invention, in which an optical fibre projects into a cavity filled with an encapsulating material, increases the effective volume of the tip geometry which allows for a number of additional, optional features. For example increasing the number of sensing elements in one sensor can increase the measured signal or facilitate the measurement of more than one analyte. A number of fibre optic sensors could be bundled together, detecting different sensors. Alternatively or additionally, a fibre optic sensor of the type described above could be combined with a different type of sensor, e.g. temperature or pressure, in the same sensing head. Additionally, the sensing tip geometry can be changed to include optimal quantities or concentrations of sensing chemistry. This chemistry could extend into the physical volume of an encapsulating polymer for example. If carefully formulated such that the dye has sufficient mobility in the encapsulating matrix, then the effects of photo bleaching may be reduced by the slow migration of dye molecules changing their position with respect to the illuminating light source.

The invention encompasses all fibre-optic based sensors in which the sensing element comprises optically active material at the distal-end of a fibre-optic. The optically active material could be such that it is fluorescent/phosphorescent, and the measurements taken are concerned with for example the rate of decay of the fluorescent or phosphorescent effect, which varies in accordance with the concentration of the assay substance. Alternatively, for example, the optically active substance could be such that its light absorption characteristics vary in dependence on the concentration of the assay substance. In that case, a colorimetric type of measurement is taken to establish the concentration of the assay substance.

The measurement of oxygen is a typical application using a fluorophor, but the invention described could also be used with other types of sensing dyes for the measurement of other analytes such as pH, ion sensing, nitric oxide sensing etc. Furthermore, sensors of the type described need not be only for clinical use since advantages also exist for other measurement scenarios. Environmental monitoring is one example where enhanced robustness and longevity of optical probes is very desirable.

Viewed from another aspect, the invention provides a method of measuring the concentration of a substance using a sensor in accordance with any of the above aspects. Viewed from a still further aspect the invention provides a combination of a sensor in accordance with any of the above aspects, with apparatus for supplying light to the optical fibre, measuring properties of light emission by the optically active substance, and calculating the concentration of the substance being analysed. Viewed from another aspect the invention provides a method of manufacturing the sensors described above.

Thus, viewed from one further aspect, the invention provides a method of manufacturing a sensor for measuring the concentration of an assay substance, comprising the steps of providing a length of optical fibre, applying to an end of the optical fibre a layer of an optically active substance whose optical properties are dependent on the concentration of the assay substance, bonding a tubular gas isolation collar to a region of the optical fibre adjacent the end of the optical fibre, the optical fibre passing through the collar in gas-tight fashion and there being an end region, including the optically active layer, projecting beyond the collar, providing an elongate needle tube connected to the gas isolation collar in gas-tight fashion, the needle tube providing a surrounding wall which defines a cavity in which the end region of the optical fibre is situated, and filling the cavity with an encapsulating material which surrounds the end region of the optical fibre.

In preferred embodiments of the invention the gas isolation collar and the needle tube are separate items bonded together during assembly, for ease of manufacture and assembly. However, in some embodiments the collar and tube could be integrally formed as a single unit or could be bonded together before assembly of the sensor.

References herein to an optical fibre encompass other equivalent types of light conveying means that may be used.

BRIEF DESCRIPTION OF THE DRAWINGS

Some embodiments of the invention will now be described by way of example and with reference to the accompanying drawings, in which.

FIG. 6 is a schematic side view in section, not to scale, of a further embodiment of a sensor in accordance with the present invention;

FIG. 7 is a schematic side view in section, not to scale, of a still further embodiment of a sensor in accordance with the present invention;

FIG. 8 is a view of a further embodiment, with two types of sensor;

FIG. 9 is a view of a modified component for use in the embodiment of FIG. 5; and FIG. 10 is a schematic view of two fibre optic sensors bundled together.

DETAILED DESCRIPTION OF THE INVENTION

Figure 1:
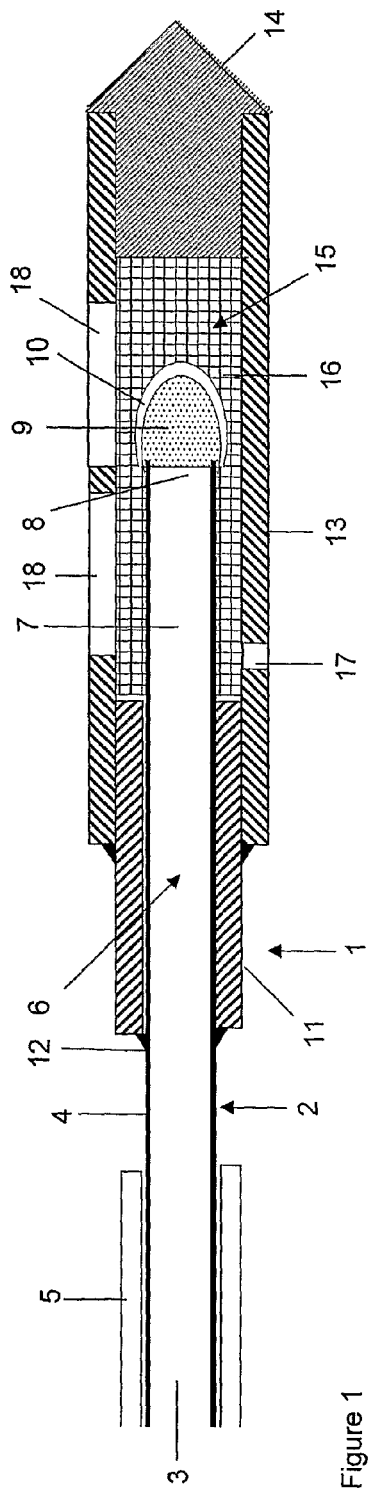
FIG. 1 is a schematic side view in section, not to scale, of a sensor in accordance with the present invention.

As shown in FIG. 1, the sensor 1 comprises a fibre optic 2 which consists of a glass fibre 3, a cladding layer 4 of silica, for example, and a protective buffer layer 5 which is provided to give strength and robustness. The buffer layer 5 has been cut back to define a terminating region 6 of the glass fibre 3 and cladding 4. This terminates in an end portion 7 having a cleaved end providing a tip 8. On this tip 8 is provided a layer 9 of a luminescent sensor material. In this particular embodiment, this material comprises a platinum complex based oxygen-sensitive indicator dye (Platinum octaethylporphyrin—PtOEP) with exponential decay life-times in the range of approximately 0.5-95.0 μS (21%-0% oxygen concentration). Platinum-based dyes exhibit excellent stability against light irradiation (i.e. low photo-bleaching), have high quantum yields and relatively long luminescence decay lifetimes compared to Ruthenium-based dyes. The Platinum complex is incorporated in silicone, polystyrene or Teflon AF (Trade Mark) or other such oxygen permeable polymer. Over the layer is 9 is an optical isolation barrier 10 containing an optical reflecting compound such as barium sulphate, titanium dioxide or other such optical reflecting dye which is mixed within a highly oxygen permeable polymer such as silicone, polystyrene or Teflon AF or another suitable oxygen permeable polymer. The optical reflector within this coating serves to increase the amount of luminescence derived signal remitted back towards the instrument for detection and subsequent signal processing. The optical isolation barrier over the tip serves to reduce the potentially deleterious effect of ambient light reaching the dye (which may cause accelerated photo-bleaching) and also reaching the optical detection system (which may cause unnecessary signal interference). The luminescence intensity as well as the luminescence decay-time increases with decreasing oxygen content—making such sensors particularly sensitive and suited to the relatively low oxygen content environments typically found in physiological media such as tissue.

A cylindrical gas isolation collar 11 is attached to the terminating region 6 of the glass fibre cladding. In practice, this is done before the layers 9 and 10 are applied to the tip 6 of the fibre. Typically for oxygen sensing, the gas isolation collar 11 is a precision-machined, tight-fitting collar manufactured from an oxygen impermeable (and MRI safe) material such as a non-ferrous metal, or a ceramic. The inside diameter of the collar 11 is such that it has a sliding-fit over the cladding layer 4 of the optical fibre. The buffer layer 5 terminates short of the gas isolation collar 11.

In manufacture, the isolation collar 11 is slipped over the fibre-optic 2 (which may be pre-cleaved or cleaved subsequently) and glued into position using an gas/oxygen impermeable adhesive, such as Permabond (Registered Trade Mark) 4E96 adhesive or Loctite (Registered Trade Mark) 4061. The adhesive is applied to the proximal end of the collar, allowing the adhesive to draw under the collar, and also form a fillet of adhesive 12 around the proximal end. Care is taken not use so much adhesive that a fillet of adhesive also forms around the distal end, and to ensure there is no adhesive spilt to the outside of the collar. The glue join must be such as to eliminate the possibility of gas transport at the cladding/collar interface.

After curing of adhesive 12, typically layers 9 and 10 are then applied to the distal end of the fibre-optic pigtail/collar assembly using conventional coating and/or dipping methods.

A cylindrical needle tube 13 of impermeable material is bonded to the gas isolation collar 11. In this embodiment, the needle tube 13 is provided with a solid, bevelled needle end 14 which is received in the end of the tube 13 and is bonded to it. A cylindrical cavity 15 is defined within the wall of the needle tube 13 between the end of the collar 11 and the needle end 14. This cavity 15 contains the end portion 7 of the fibre optic, and is filled with a polymer encapsulating material 16 which completely surrounds portion 7 and the sensor layers 9 and 10. A small bleed hole 17 in the side of the needle tube helps with filling cavity 15.

The needle tube 13 provides a mechanical barrier/sheath over the fragile optical fibre, providing rigidity, strength and ease of insertion into tissue. By mechanically confining the sensing tip, this construction substantially reduces the risk of mechanical damage to the sensing tip and in particular substantially reduces the risk of the sensing tip detaching from the distal end of the fibre when used in tissue.

Elongate lateral apertures 18 are provided in the needle tube 13, communicating the interior of the cavity 15, filled with encapsulating material 16, with the exterior of the sensor. The apertures are arranged as three groups of two longitudinally arranged apertures 18, the groups being arranged at equal intervals around the circumference of the needle tube 13. The apertures are laser cut, for example, in the wall of the needle tube 13, which is otherwise impermeable.

Typically, for oxygen sensing applications, the needle tube 13 can be manufactured from oxygen impermeable materials such as steel. Non ferrous metals and ceramics would be used for MRI-safe applications. A preferred material is titanium.

The construction sequence continues with fitting the needle tube 13 over the gas isolation collar 11 (suitably dimensioned such that a sliding-fit is obtained) and cementing in place over the isolation collar using an adhesive (e.g. Permabond 4E96 or Loctite 4014) which will substantially resist permeation of substances such as oxygen. The needle tube 13 is pre-fitted with the solid bevelled end 14, the bevel-ended geometry being such as to facilitate insertion of the needle probe into tissue. The cavity 15 is externally sealed with a section of suitable covering (e.g. heat-shrink tubing) in order to prevent the encapsulant from draining-out during the filling and curing processes. It is then filled with a suitable gas permeable polymer 16 via the side-window apertures 18. Typically for oxygen sensing, this would be a highly permeable polymer (e.g. Nusil 6010 silicone or Teflon AF or a fluorosilicone) type compound that has been thoroughly degassed prior to application. The small bleed-hole 17 in the needle tube 13 enables entrapped air to be expelled from the cavity 15 during the cavity filling process. Finally, the covering is removed when the encapsulant has cured.

The optical isolation barrier 10 also operates as a chemical isolation barrier, and indeed in alternative embodiments could perform only that function and not contain a reflecting compound. The chemical barrier prevents the migration of the encapsulant material into the sensing tip 9, this being a particular problem when the encapsulant is being cured and short lived contaminants may be produced, and also prevents migration of the sensing chemistry from the tip 9 into the encapsulant. The chemical barrier is preferably of a silicone having good barrier properties and could for example be a fluoro silicone. Other substances could be a dried hydrogel, ethyl cellulose, and the Teflon AF already mentioned. The thickness of the isolation barrier 10 may be increased over that required for optical isolation, to improve the effectiveness of chemical isolation.

In this embodiment, the cavity volume formed from the position of the leading edge of the gas isolation collar 11 to the start of the needle end 14, minus the volume of the end portion 7 of the optical fibre in this section, will determine the total volume of the encapsulated polymer 16. This volume, combined with permeability of the encapsulant will determine the overall response time of the sensor to a change in partial pressure of the analyte being measured. The area of the open tube in contact with the tissue will determine the effective sampling area of the sensor.

The bleed-hole 17 is an optional aspect of the designs and is included as a way to ease probe construction.

The viscosity of the encapsulant should be chosen to facilitate the manufacturing process.

In this embodiment, sensing takes place along the side of the needle tube 13 at a point or points distant from the distal end of the needle, using a closed-end needle construction. This type of design has the advantage of providing a means of sensing at a known distance away from the site of maximal tissue trauma. This type of construction also provides a mechanical barrier/sheath over the (typically fragile) optical fibre, offering rigidity, strength and ease of insertion into tissue. By mechanically confining the entire sensing tip, this construction substantially reduces the risk of mechanical damage to the sensing tip and in particular substantially reduces the risk of the sensing tip detaching from the distal end of the fibre when used in tissue.

In this embodiment, the cavity volume formed from the position of the leading edge of the gas isolation collar with respect to internal trailing edge of the solid bevel needle end, minus the volume of the optical fibre in this section, will determine the total volume of the polymer encapsulated cavity. This volume, combined with permeability of the encapsulant will determine the overall response time of the sensor to a change in partial pressure of the analyte being measured. The total area of the side-window aperture(s) in contact with the tissue will determine the effective overall sampling area of the sensor.

Figure 2:
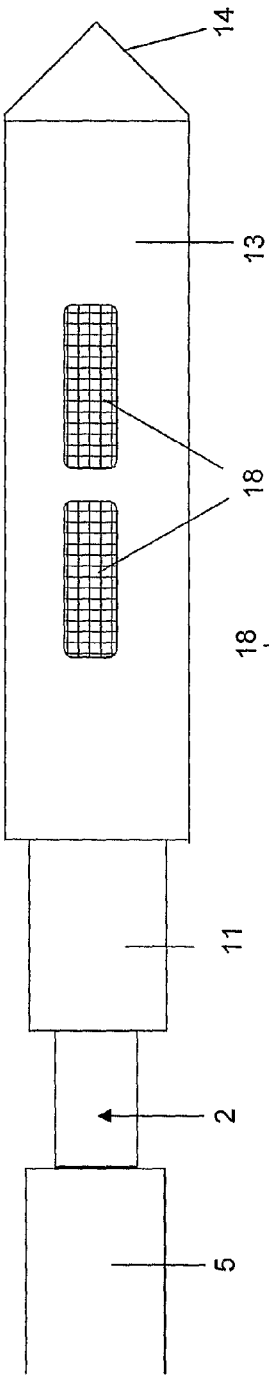
FIG. 2 is a top view of the sensor of FIG. 1.
Figure 3:
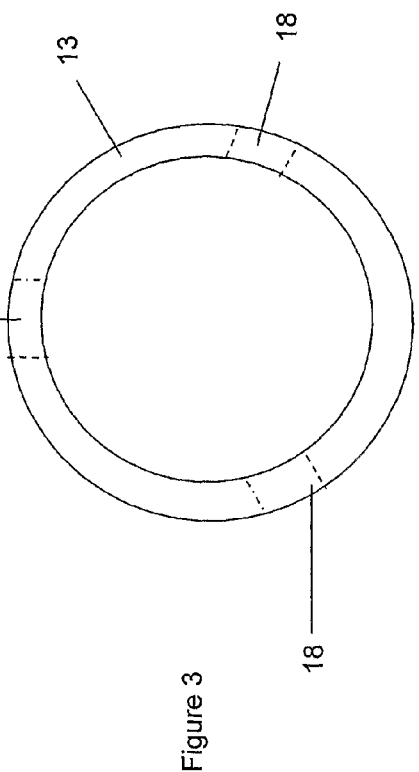
FIG. 3 is an end view of part of the sensor of FIG. 1.
Figure 4:
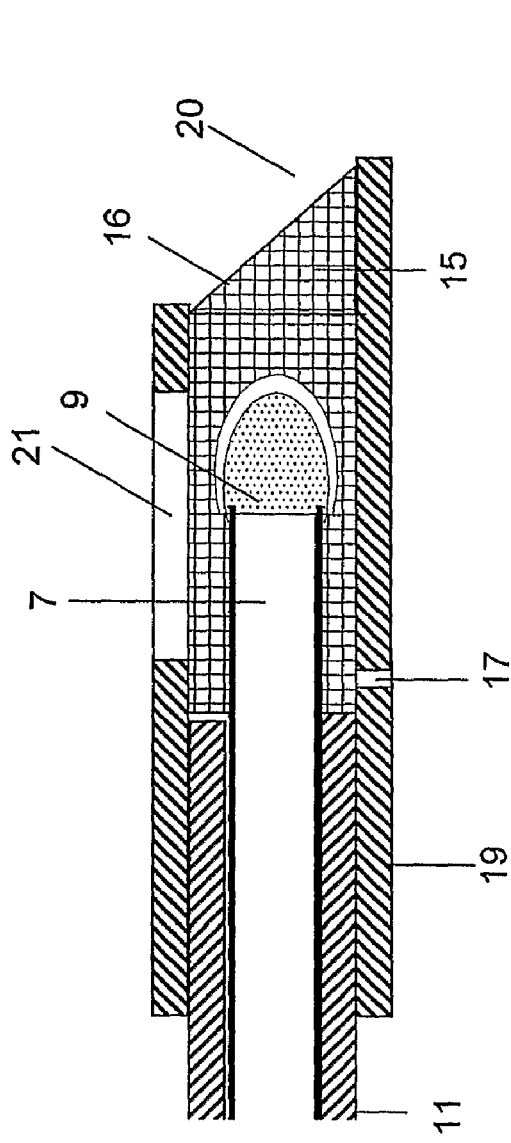
FIG. 4 is a section through part of a modification of the embodiment of FIG. 1.

FIG. 4 shows a modified arrangement which otherwise is generally similar to the arrangement of FIGS. 1 to 3. In this embodiment, a modified impermeable needle tube 19 is bonded to the gas isolation collar 11, the needle tube having a bevelled open-tube end 20 and three equi-angularly spaced lateral apertures 21. The bevel-ended geometry is such as to facilitate insertion of the needle probe into tissue. The construction sequence is analogous to that of the embodiment of FIGS. 1 to 3. In this embodiment sensing takes place through the lateral apertures 21 and the open end 20. The area of the (e.g. oval) shape formed at the open bevelled end 20 in contact with the tissue, and the combined area of the lateral apertures 21 will determine the effective sampling area of the sensor.

Figure 5:
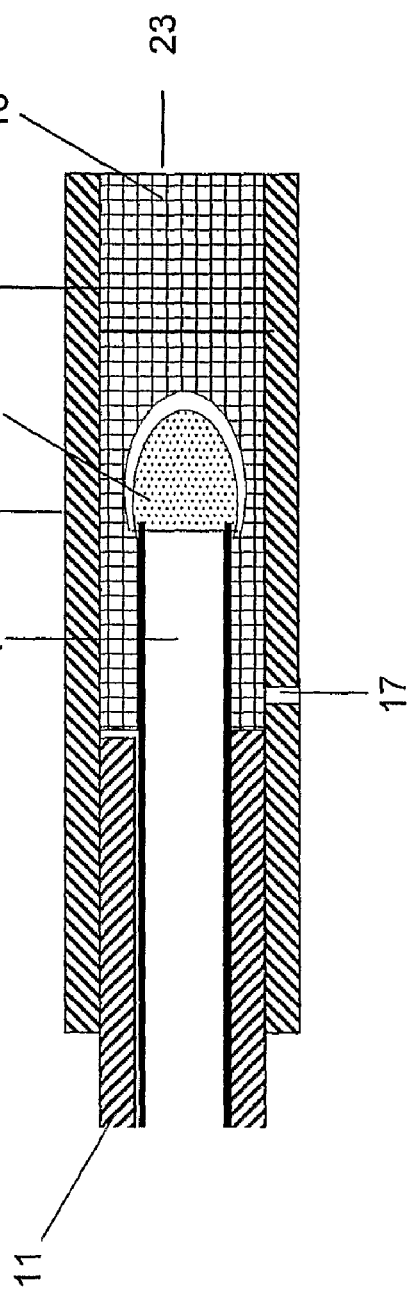
FIG. 5 is a section through part of a second modification of the embodiment of FIG. 1.

FIG. 5 shows a further modified arrangement, which otherwise is generally similar to the arrangement of FIGS. 1 to 3. In this embodiment, a modified needle tube 22 is bonded to the gas isolation collar 11, the needle tube having a straight cut open-tube 23. The construction sequence is analogous to that of the embodiment of FIGS. 1 to 3. In this embodiment sensing takes place only through the open end 23 and the circular area of the open end 23 in contact with the tissue will determine the effective sampling area of the sensor. The needle tube 22 is impermeable.

In a further modification of the embodiment of FIG. 5, the needle tube 22 may be made of permeable material, so that sampling can take place over the entire circumference of the wall bounding the cavity 15. In this embodiment, an integrating type sensor is constructed such that the sensing, or measurement, takes place across the entire area of a gas permeable tube that is in contact with the tissue. This type of design has the advantage of providing a means of determining and increasing the effective sampling area of the sensor without massively increasing the overall fibre diameter, which is undesirable because of increased tissue trauma. By obtaining sensing activity substantially from an area formed by a tubular section of suitable gas permeable material, most of the sensing takes place at distances away from the distal end of the probe i.e. away from the site of maximal tissue trauma. The gas permeable tube also provides a mechanical barrier/sheath over (the typically fragile) optical fibre based sensor offering increased strength and rigidity. By mechanically confining the entire sensing tip, this construction substantially reduces the risk of mechanical damage to the sensing tip and in particular substantially reduces the risk of the sensing tip detaching from the distal end of the fibre when used in tissue.

For oxygen sensing, the gas permeable tube 22 can be formed from a highly oxygen permeable tubular-formed polymer or membrane material such as Teflon® AF or silicone rubber. Less oxygen permeable materials/membranes could also be deployed that, have as part of their function, dense matrices of small holes providing a means for oxygen transport through the material.

It will be appreciated that the permeable tube 22 could be provided with a closed end.

In the embodiments of FIGS. 4 and 5, the cavity volume 15 formed from the position of the leading edge of the gas isolation collar 11 to the open end of the needle tube 19 or 22, minus the volume of the optical fibre end portion 7, determines the total volume of the polymer encapsulated cavity. This volume, combined with permeability of the encapsulant, will determine the overall response time of the sensor to a change in partial pressure of the analyte being measured.

FIG. 6 is a modification of the embodiment of FIGS. 1 to 3, using a modified gas isolation collar 24 which is similar to collar 11 but includes an integral radially directed shoulder 25. This arrangement can be used with the embodiments of FIGS. 4 and 5 also, and may be of particular use with the permeable tube variant of FIG. 5. The modified gas isolation collar provides a further isolation barrier. Typically, for oxygen sensing applications, the modified gas isolation collar isolates everything forward of the shoulder such that apertured or gas permeable needle tube is prevented from contacting any other tubing or sheathing materials that may also be permeable to oxygen and which could otherwise provide an artefactual source of oxygen that would adversely affect the integrity of the oxygen measurement. The modified gas isolation collar 24 is a precision machined component manufactured from a suitable oxygen impermeable (and MRI safe) material such as a non ferrous metal or ceramic.

In this embodiment, fibre-optic cable sheathing 26 is positioned over the modified gas isolation collar 24 and cemented in place using conventional bonding techniques. Such sheathing may also be used with the other embodiments.

FIG. 7 illustrates a modification of the embodiment of FIG. 1. In this arrangement the needle tube comprises a base, or proximal, part 27 and a distal part 28. These are both bonded to the gas isolation collar 11, and adhesive 29 also bonds the parts 27 and 28 to each other and to the collar 11. The construction sequence begins with fitting the base needle tube part 27 over the gas isolation collar 11 (suitably dimensioned such that a sliding-fit is obtained) and cementing it in place over the isolation collar using an oxygen impermeable adhesive (e.g. Permabond 4E96 or Loctite 4014). For additional strength and adhesion, the base needle tube part 27 could be back-filled with a suitable structural gap-filling adhesive. The section of distal needle tube 28, complete with side-window aperture(s) and pre-fitted with a solid bevelled end, is then cemented to the other half of the gas isolation collar 11 in a similar fashion, and to proximal part 27. The distal needle section is then filled with a suitable gas permeable polymer via the side-window aperture(s). Typically for oxygen sensing, this would be a highly permeable polymer (e.g. Nusil 6010 silicone or Teflon AF) type compound that has been thoroughly de-gassed prior to application.

FIG. 8 shows an alternative type of sensor 29. This has a modified gas isolation collar 30 and needle tube 31. The needle tube has a lateral aperture 32, communicating with a cavity 15 containing encapsulant 16 in which is embedded the sensing tip 9 of a fibre optic 2 whose construction is as described previously. The cavity is closed off by an end plug 33 bonded to the surrounding wall defined by the tube 31. The tube 31 extends beyond the end plug 33 to a needle tip 34 whose inner end is spaced from plug 33 to define a chamber 35. A lead 36 passes through collar 30 in sealing fashion, through encapsulant 16, and through end plug 33 in sealing fashion to chamber 35, where it is connected to a sensor 37 which may for example measure temperature or pressure. Aperture 38 is provided, communicating chamber 35 with the outside of the sensor. The size and design of this aperture 38 will depend on the type of sensor 37, and for example would be larger for a pressure sensor. Although in this case the chamber 35 is distal with respect to cavity 15, in an alternative arrangement it could be proximal.

FIG. 9 shows a component 39 in which the gas isolation collar 11 and the needle tube 22 are combined as an integral unit. This can be used instead of the separate components in the embodiment of FIG. 5, and a corresponding modification can be made to the other embodiments.

FIG. 10 shows how instead of a single fibre optic 2, there can be a bundle 40 of two or more fibre optics 2, each having a sensing tip 9 whose sensing chemistry is selected for a different analyte, or for example the same analyte using different ways.

In use of a sensor as described above, in accordance with any of the embodiments, the sensor is positioned to measure the concentration of oxygen in a portion of tissue. An appropriate light source, such as an LED driven as required, applies light to the fibre optic to activate the fluorophor, and a detector detects light emitted by the fluorophor and generates a corresponding signal. The signal is analysed and the concentration of oxygen is calculated. In one arrangement, the detector may detect transient changes in light simultaneously with the pumping light source operating to apply light to the optical fibre.

Significant features of probe sensors in accordance with the various embodiments of the invention include:

Producing an integrated or averaged measurement over an optimised sensing area or volume.

Controlling and optimising the sensing area/volume of the sensing measurement.

Providing a protective mechanical barrier/sheath over an optical fibre based sensor, which also provides a protective environmental barrier/sheath, against ambient light, ionic contamination and so forth.

Providing a gas isolation collar.

Providing a sensor for external or surface measurements, which seals around the sensing area such that ambient interference is eliminated or minimised.

Providing a probe for insertion that locates sensing at a significant distance away from the site of maximal tissue trauma.

Providing control over the measurement rate and response times of sensors by the inclusion of inert impermeable fillers in the permeable tip construction.

Providing a probe where the sensing element is formed by the whole polymer volume in the probe, allowing for additional luminophor to be included, thereby minimising photobleaching and/or prolonging probe lifetime.

Providing means to isolate the sensing element from other sources of analytes, which might otherwise produce interference or artefacts.

Providing means for protecting the sensing element from transient temperature fluctuations.

Providing a means of sensor construction that is MRI safe.

Providing a sensor construction that provides for ease of assembly.

Providing a probe with multiple fibres, e.g. for different sensing purposes, terminating in the sensing volume within the cavity.

Providing a probe with multiple sensing elements/dyes in the termination housing.

Providing for additional active ingredients other than the primary luminophor.

Providing a platinum complex based luminescent dye for sensing oxygen.

Providing means for immobilising a platinum complex dye on the distal-end of a fibre-optic.

Providing an optical reflection layer and optical isolation barrier around a luminescent dye sensor.

The invention further encompasses the use of any of these features, alone or in any workable combination, and is not restricted to the particular aspects identified or claimed.

The invention claimed is:

1. A sensor for measuring the concentration of an assay substance, the sensor comprising an optical fiber which extends longitudinally into a cavity defined by a surrounding wall, the optical fiber having an end portion within the cavity, the end portion terminating in a tip which is provided with an optically active substance which has optical properties which depend on the concentration of the assay substance; wherein the cavity is filled with an encapsulating material which is permeable to the assay substance and which encapsulates the end portion of the optical fiber, and the surrounding wall is provided with at least one flow path for communicating the cavity with a region to be sampled; and wherein the optical fiber includes a glass fiber and an outer buffer layer, a terminating portion of the optical fiber is devoid of the buffer layer, the terminating portion of the optical fiber passes through a gas isolation collar and into the cavity, the gas isolation collar being bonded to the terminating portion of the optical fiber in substantially gas-tight fashion, and the buffer layer terminating short of the gas isolation collar.

2. A sensor as claimed in claim 1, wherein the surrounding wall of the cavity is substantially impermeable and the or each flow path is provided by an aperture in the surrounding wall.

3. A sensor as claimed in claim 2, wherein the aperture is in the form of an elongate slot.

4. A sensor as claimed in claim 1, wherein the surrounding wall of the cavity is substantially impermeable and the or each flow path is provided by a permeable region in the surrounding wall.

5. A sensor as claimed in claim 1, wherein a plurality of flow paths are provided, spaced circumferentially around the surrounding wall.

6. A sensor as claimed in claim 1, wherein the surrounding wall of the cavity is substantially permeable so as to provide flow paths.

7. A sensor as claimed in claim 1, wherein the encapsulating material is a gas permeable polymer.

8. A sensor as claimed in claim 1, wherein the encapsulating material comprises permeable and impermeable components.

9. A sensor as claimed in claim 1, wherein the optical fiber comprises a cladding layer between the glass fiber and the buffer layer.

10. A sensor as claimed in claim 1, wherein the cavity surrounding wall is defined by a tube which is connected to the gas isolation collar in substantially gas-tight fashion.

11. A sensor as claimed in claim 10, wherein the tube comprises separate proximal and distal portions which are bonded to the gas isolation collar and to each other in substantially gas-tight fashion.

12. A sensor as claimed in claim 1, wherein the gas isolation collar is elongate.

13. A sensor as claimed in claim 1, wherein the gas isolation collar is provided with a radially outwardly projecting shoulder.

14. A sensor as claimed in claim 1, wherein a fiber optic cable sheath is provided over the optical fiber and engages the gas isolation collar.

15. A sensor as claimed in claim 1, wherein the distal end of the cavity is open.

16. A sensor as claimed in claim 1, wherein the distal end of the cavity is closed.

17. A sensor as claimed in claim 1, wherein the cavity is substantially filled to capacity with the encapsulating material.

18. A sensor as claimed in claim 1, wherein the end portion of the fiber optic within the cavity is spaced from the surrounding wall of the cavity by encapsulating material.

19. A sensor as claimed in claim 1, adapted for use in measuring the concentration of oxygen in tissue.

20. A sensor as claimed in claim 1, wherein the optically active substance on the tip of the optical fiber is provided with a chemical barrier between the optically active substance and the encapsulating material.

21. A sensor as claimed in claim 1, wherein the optically active substance on the tip of the optical fiber is provided with a reflective optical barrier between the optically active substance and the encapsulating material.

22. A sensor as claimed in claim 1, wherein a plurality of optical fibers are provided, each with a tip on which is coated a different optically active substance for detecting a different assay substance.

23. A sensor as claimed claim 1, wherein in addition to an optical fiber provided with a tip with an optically active substance, the sensor includes a different type of sensing element.

24. A sensor as claimed in claim 1, wherein the optically active substance exhibits fluorescent or phosphorescent activity which depends on the concentration of the assay substance.

25. A sensor as claimed in claim 1, wherein the optically active substance has colorimetric properties which depend on the concentration of the assay substance.

26. A sensor as claimed in claim 1, in combination with apparatus for supplying light to the optical fiber, measuring properties of light emitted by the optically active substance, and calculating the concentration of the assay substance being analysed.

27. A method of measuring the concentration of an assay substance, the method comprising:

providing a sensor comprising an optical fiber which extends longitudinally into a cavity defined by a surrounding wall, the optical fiber having an end portion within the cavity, the end portion terminating in a tip which is provided with an optically active substance which has optical properties which depend on the concentration of the assay substance; wherein the cavity is filled with an encapsulating material which is permeable to the assay substance and which encapsulates the end portion of the optical fiber, and the surrounding wall is provided with at least one flow path for communicating the cavity with a region to be sampled, and wherein the optical fiber includes a glass fiber and an outer buffer layer, a terminating portion of the optical fiber is devoid of the buffer layer, the terminating portion of the optical fiber passes through a gas isolation collar and into the cavity, the gas isolation collar being bonded to the terminating portion of the optical fiber in substantially gas-tight fashion, and the buffer layer terminating short of the gas isolation collar;

providing an apparatus for supplying light to the optical fiber, measuring properties of light emitted by the optically active substance, and calculating the concentration of the assay substance being analysed.

28. A method as claimed in claim 27, used for measuring oxygen concentration in tissue.

29. A sensor as claimed in claim 1, wherein a tubular member is connected to the gas isolation collar, so that the end of the gas isolation collar provides an end wall of the cavity through which the end portion of the optical fiber passes in sealing fashion, and the tubular member provides the surrounding wall defining the cavity in which the end portion of the optical fiber is enclosed.

30. A sensor for measuring the concentration of an assay substance, the sensor comprising:

an optical fiber comprising an inner glass fiber and an outer buffer layer, the buffer layer terminating short of an end of the glass fiber so as to define a buffer free end portion;

a tubular member and a gas isolation collar, the collar extending into the tubular member and being sealed thereto in substantially gas tight fashion; the tubular member defining a surrounding wall of a cavity, and an end of the gas isolation collar defining a base of the cavity;

wherein the buffer free end portion of the optical fiber extends longitudinally through the gas isolation collar into the cavity, the gas isolation collar being bonded to the buffer free end portion in substantially gas-tight fashion;

wherein the buffer free end portion terminates in a tip which is provided with an optically active substance which has optical properties which depend on the concentration of the assay substance; and wherein the cavity is filled with an encapsulating material which is permeable to the assay substance and which encapsulates the buffer free end portion of the optical fiber in the cavity, and the surrounding wall is provided with at least one flow path for communicating the cavity with a region to be sampled.

\* \* \* \* \*